United States Patent [19]

Johnson

[11] Patent Number: 4,532,231

[45] Date of Patent: Jul. 30, 1985

[54] PROCESS FOR PRODUCING A CATALYST

[75] Inventor: David W. Johnson, Stockton-on-Tees, England

[73] Assignee: Imperial Chemical Industries PLC, Great Britain

[21] Appl. No.: 579,645

[22] Filed: Feb. 13, 1984

[30] Foreign Application Priority Data

Feb. 21, 1983 [GB] United Kingdom ................. 8304749

[51] Int. Cl.³ .......................... B01J 23/02; B01J 23/50
[52] U.S. Cl. ..................................... 502/347; 549/537
[58] Field of Search ....................... 502/243, 347, 348; 549/537

[56] References Cited

U.S. PATENT DOCUMENTS

| 4,033,903 | 7/1977 | Maxwell | 502/347 |
| 4,361,504 | 11/1982 | Solomon et al. | 502/348 |
| 4,400,308 | 8/1983 | Alter et al. | 502/347 X |

Primary Examiner—W. J. Shine
Attorney, Agent, or Firm—Cushman, Darby & Cushman

[57] ABSTRACT

A catalyst for the production of alkylene oxides is produced by impregnating a supported silver composition with a solution of an alkali metal compound. The uniformity of alkali metal distribution is improved by including in the solution at least 20% by weight of a heavy component which is subsequently removed by chemical reaction.

8 Claims, No Drawings

PROCESS FOR PRODUCING A CATALYST

This invention relates to catalysts and their production.

It is known to use catalysts comprising silver and alkali metal on a porous support in a process in which an olefine, for example propylene or preferably ethylene is oxidised with oxygen to produce an alkylene oxide. Such catalysts may be produced by depositing silver on the support (for example by introducing a silver compound as a suspension or solution in a liquid, evaporating the liquid and decomposing the silver compound to silver) and subsequently impregnating the support with a solution of an alkali metal compound, the solution then being evaporated.

It has been found that when alkali metal compounds are introduced in this way there is a tendency to deposit high concentrations of alkali metal compound on the outer parts of the pellets of the catalysts and less on the inner ones, probably because of migration of the solution to the external surfaces of catalyst pellets from which the evaporation takes place. Thus one does not obtain a desired optimum concentration of alkali metal compound throughout the catalyst and the performance of the catalyst may suffer because most regions are covered with an inappropriate amount of alkali metal compound.

According to this invention a catalyst for the production of alkylene oxides, for example propylene and preferably ethylene oxide, is produced by impregnating a composition comprising silver supported on a porous heat resisting support with a solution of an alkali metal compound in a liquid which comprises a solvent for the alkali metal compound which comprises at least 20% preferbly at least 25% and more preferably at least 30% by weight of a component which preferably has a melting point at atmospheric pressure above 50° C. and more preferably above 100° C. and which can be converted by chemical reaction for example oxidation to gas or vapour only at a temperature below its boiling point, or a substance capable of forming such a component before evaporation, and removing the said component by chemical reaction, the boiling point of the said component being higher, preferably at least 20° C. and more preferably at least 50° C. higher than the temperature of the said chemical reaction under the reaction conditions.

The viscosity of the solution is preferably below 0.5 Pas for example $5 \times 10^{-4}$ to $5 \times 10^{-1}$ Pas and preferably $10^{-3}$ to $10^{-1}$ Pas at the impregnation temperature which is suitably in the range 10° to 100° C. and is preferably 15° to 40° C.

The removal by chemical reaction may comprise for example hydrolysis with steam followed by evaporation, or polymerisation or decomposition to carbonaceous residues or otherwise forming a solid or a viscous solution followed by oxidation. When the chemical reaction is oxidation the component preferably has a boiling point at the pressure at which the oxidation is carried out of at least 250° C. Preferably it has a boiling point of at least 250° C. at atmospheric pressure when the oxidation is carried out at a higher pressure.

The liquid may comprise only the said component and the compound. Suitable components include organic acids, especially $C_{10}$ to $C_{20}$ carboxylic acids or lactic acid. If any additional diluent is present it preferably boils at a temperature below that of the said component preferably at least 50° C. below at atmospheric pressure.

Preferably at most 70% and more preferably at most 50% of the said component is present. The component may be for example a xanthan gum, a polyethylene or polypropylene glycol having a molecular weight in the range 200 to 100,000 and preferably 1,000 to 20,000, a polyvinyl alcohol, a partially hydrolysed carboxylated cellulose, a sugar, for example sucrose or glucose, glycerol or other poly-hydroxy compounds suitably those in which at least 2 hydroxy groups are present per 3 carbon atoms and which suitably contain at least 5 carbon atoms. The solution suitably comprises at least 25% and preferably at least 40% of a volatile solvent for the alkali metal compound, for example a lower alcohol suitably a $C_1$ to $C_4$ alcohol, water or a mixture thereof for example a mixture of methanol and water.

The alkali metal compound is suitably a carbonate bicarbonate, hydroxide or carboxylate for example a formate, acetate or lactate or preferably an oxalate. It is preferred not to use the alkali metal halides as interaction between the silver content of the catalyst and the halide ions is believed to be possible and this may complicate the preparation or conditioning of the catalyst, and to avoid the use of salts from which elements which are not readily removed from the catalyst are present for example phosphate and sulphate salts. The preferred alkali metals are sodium, potassium, rubidium or cesium especially potassium, rubidium and/or cesium and combination of cesium and/or rubidium with sodium and/or preferably potassium.

Silver may be introduced to a pre-formed porous heat resisting support as a suspension of silver or silver oxide in a liquid medium for example water or by impregnation of the support with a solution of a silver compound which can be reduced to silver metal if necessary by means of a reducing agent for example hydrogen. If necessary a heat treatment may be used to decompose the silver compound to silver. Suitably the impregnating solution contains a reducing agent which may be for example an anion, for example a formate, acetate, propionate, lactate, tartarate or preferably oxalate ion, of a silver compound in the solution. The reducing agent may be for example an aldehyde, for example formaldehyde or acetaldehyde or an alcohol preferably having 1 to 4 carbon atoms for example methanol or ethanol.

The solution may be a solution in water and/or an organic solvent, for example an aliphatic alcohol preferably having 1 to 4 carbon atoms, a polyhydric alcohol for example ethylene glycol or glycerol, a ketone for example acetone, an ether for example dioxan or tetrahydrofuran, a carboxylic acid for example acetic acid, or molten lactic acid which is preferably used in the presence of water, or an ester for example ethyl acetate or a nitrogen containing base for example pyridine or formamide. An organic solvent may function as a reducing agent and/or complexing agent for the silver also.

If the silver is introduced by impregnating a support with a solution of a decomposable silver compound it is preferred that ammonia and/or a nitrogen containing base should be present. The nitrogen containing base suitably acts as a ligand maintaining the silver in solution; for example it may be pyridine, acetonitrile, an amine, especially a primary or secondary amine having 1-6 carbon atoms, or preferably ammonia. Other suitable nitrogen-containing bases include acrylonitrile, hydroxylamine and alkanolamines for example ethanolamine, alkylene diamines having from 2-4 carbon atoms or amides for example formamide or dimethyl formamide. The nitrogen-containing bases may be used alone or in admixture, mixtures of ammonia and a second nitrogen containing base being preferred. Suitably the nitrogen containing base or bases are used together with water.

Alternatively the solution may be a neutral or acid solution for example it may be a solution of a silver carboxylate especially a formate, acetate, propionate, oxalate, citrate, tartarate or preferably lactate or for example a solution of silver nitrate.

The solutions preferably contain 3-50% of silver by weight.

Impregnation may be carried out in a single stage or if desired may be repeated one or more times. By this means higher silver contents of the catalyst may be achieved.

The silver compound may generally be reduced to silver by heating in the range 100° to 350° C., for example for a perod of 15 mins to 4 hours, preferably in the substantial absence of oxygen, for example in the presence of an inert gas for example nitrogen.

The catalyst support preferably has an apparent porosity as measured by the mercury absorption method of at least 20%, for example 30-80% preferably 30-65% and more preferably 40-60% and mean pore diameters of 0.1 to 20 microns preferably 0.3 to 4 microns as measured by the mercury porosimetry method. The pore size distributions of the support may be bimodal, in which case the smaller pores preferably account for at least 70% of the total pore volume and have a mean pore diameter preferably in the range 0.1 and preferably 0.3 to 4 microns, and the larger pores preferably have a mean pore diameter in the range 25 to 500 microns.

Most of the silver content of the catalyst is preferably present in the form of discrete particles adhering to the support having equivalent diameters of less than 10,000A preferably in the range 20-10,000A and more preferably 40-8,000A. By equivalent diameter is meant the diameter of a sphere of the same silver content as the particle.

Preferably at least 80% of the silver is present as particles having equivalent diameters in the aforesaid range, the quantity of silver being judged in terms of the number of particles falling in that range. The silver may be present as silver and/or silver oxide and is thought to be present normally as silver particles having a surface layer of silver oxide. The dimensions of the silver particles may be determined by scanning electron microscopy.

The support may be an alumina, silicon carbide, silica, zirconia or silica/alumina support, but it is preferably composed of an aggregate of alpha-alumina particles which may be fused together or cemented together with, for example silica or baryta.

The catalyst preferably comprises 3 to 50% and more preferably 5 to 20% by weight of silver.

The catalyst suitably comprises at least 0.002 gram equivalents and preferably at least 0.003 gram equivalents and preferably at most 0.04 and more preferably at most 0.016 equivalents of cesium and/or rubidium on the surface of the support per kilogram of the total catalyst. The amount of cesium is suitably in the range 250 to 3,000 and preferably 400 to 1,500 parts per million by weight per square meter of support surface area. The amount of rubidium is suitably in the range 180 to 2,000 and preferably 300 to 1,000 parts per million by weight per square meter of support surface area. By parts per million is meant parts per million by weight cesium and/or rubidium expressed as the element based on the total weight of the catalyst.

The total concentrations of alkali metals in water extractable form are preferably from 200 to 10,000, preferably 300 to 5,000 parts per million by weight potassium, from 300 to 20,000 and preferably 500 to 10,000 parts per million by weight of sodium, 400 to 4,000 and preferably 500 to 2,000 parts per million by weight of cesium or 250 to 2,500 and preferably 400 to 1,500 parts per million by weight of rubidium.

Any alkali metal compounds present as components of the support in non water extractable form are ignored as they do not contribute to catalysis.

The catalyst may be used in the production of ethylene oxide in known processes, for example those of our European patent application Nos. 57,066 and 3,642.

EXAMPLE 1

A support in the form of hollow 8 mm long, 8 mm external diameter, 3 mm internal diameter cylinders composed of α-alumna and containing 0.4% silica, of surface area 2.1 $m^2g^{-1}$ (measured by mercury porosimetry) and pore volume 0.30 $cm^3 g^{-1}$ was impregnated with a solution of silver nitrate/isopropylamine/water (0.30 g Ag per ml, concentration of isopropylene=2.1 g mol per g mol silver and water to make up volume) for 20 minutes at ambient temperature. The excess solution was drained off the pellets and then the pellets were dried at 90° C. in nitrogen for 3 hours after which the temperature was raised in steps to 240° C. over 8 hours. Finally the material was heated at 240° C. for 1 hour.

This material was allowed to cool and then washed with distilled water at 95° C. at a liquid space velocity of 4 liters/kg catalyst/hour for 16 hours. The catalyst was then dried at 120° C. for 2 hours. This material is designated catalyst A.

Catalyst A was impregnated with a solution containing cesium oxalate in a solvent containing 50 g/100 ml polyethylene glycol, mean molecular weight 4,000, and methanol to volume. The volume of solution used was 1.1 times that required to fill the pores of the catalyst, the concentration of cesium was 3.213 g/liter and the impregnation was continued for 15 hours. After this time the excess liquid was drained off and the catalyst dried at 120° C. for 1 hr under an atmosphere of nitrogen. This is catalyst B. The catalyst contained 874 ppm cesium by weight.

EXAMPLE 2

0.4 g catalyst B were loaded into a stainless steel reactor tube, internal diameter 2 mm and tested for ethylene oxidation activity. The following gas composition was employed: 30% ethylene, 8% oxygen, 0.6% ethane, 4% carbon dioxide, 1.0 ppm vinyl chloride and the balance nitrogen, total pressure=16 atmospheres, gas flow rate=3,000 l/l catalysts/hr (expressed at standard temperature and pressure). The temperature was adjusted until a percentage conversion of oxygen of 40% was achieved. The catalyst stability was monitored over 52 days. The selectivity, temperature, and rates of change of these are shown in Table 1.

EXAMPLE 3 (Comparative)

Catalyst A was impregnated with cesium as in Example 1 except that the polyethylene glycol was omitted and extra methanol used to make up the volume. The concentration of cesium in the solution was 3.57 g/liter. This catalyst (C) was tested in the manner described in Example 2. The results of this test are shown in Table 1. Catalyst C gave the same initial performance as catalyst B but lost selectivity at three times the rate and required a temperature rise of almost double the rate of catalyst B.

TABLE 1

| Catalyst | Selectivity (initial) (%) | Temperature (initial) (°C.) | Selectivity Fall (%/day) | Temperature Rise (°C./day) |
|---|---|---|---|---|
| B | 79.5 | 212 | 0.05 | 0.37 |
| C (comparative) | 79.5 | 210 | 0.15 | 0.68 |

EXAMPLE 4

Catalyst A was impregnated with cesium as described in Example 1 except that the cesium concentration was 2.14 g/liter and the volume of solution ws 4.5 times that needed to fill the pores of the support. The catalyst (D) contained 763 ppm cesium. Its performance is shown in Table 2.

EXAMPLE 5 (Comparative)

Catalyst E was prepared in the same way as catalyst D except that PEG 4,000 was omitted and the volume made up with methanol and the cesium concentration was 1.2 g/liter. The catalyst contained 890 ppm cesium. The performance of this catalyst is shown in Table 2. Whilst catalyst E was initially more selective than catalyst D the former lost selectivity at 8 times the rate of catalyst D such that their selectivities were equal after 12 days. After this time catalyst E continued to lose selectivity at the same high rate. After 37 days its selectivity had fallen to 74.8% from an initial value of 79.8%. The temperature rise of catalyst E was double that of catalyst D.

TABLE 2

| Catalyst | Selectivity (initial) (%) | Temperature (initial) (°C.) | Selectivity Fall (%/day) | Temperature Rise (°C./day) |
|---|---|---|---|---|
| D | 78.9 | 208 | 0.021 | 0.45 |
| E (comp) | 79.8 | 207 | 0.172 | 1.04 |

EXAMPLE 6

A series of catalysts was prepared from catalyst A containing different levels of cesium, by the methods described in Example 1, by varying the cesium content of the impregnation solution. These catalysts F-Q were tested as described in Example 2. The results of these tests are shown in Table 3.

TABLE 3

| Catalyst | [Cs] (ppm) | Initial Performance Selectivity (%) | Initial Performance Temperature (°C.) | Stability Selectivity Fall (%/d) | Stability Temp Rise (°C./d) |
|---|---|---|---|---|---|
| F | 695 | 78.4 | 204 | | |
| G | 755 | 79.0 | 204 | | |
| H | 953 | 79.5 | 218 | | |
| I | 992 | 79.7 | 219 | | |
| J | 1090 | 78.2 | 224 | | |
| K | 900 | 80.0 | 214 | 0.045 | 0.55 |
| L | 730 | 78.5 | 206 | | |
| M | 1140 | 79.2 | 218 | 0.046 | 0.34 |
| N | 830 | 79.4 | 207 | 0.041 | 0.31 |
| P | 1010 | 79.3 | 219 | 0.071 | 0.34 |

EXAMPLE 7

A number of catalysts prepared following the methods described in Examples 1 and 3 were analysed for their radial distribution of cesium by taking 5 cylindrical annular sections from the hollow cylindrical pellets and analysing. The cesium analyses of these catalysts are shown in Table 4. The normalised standard deviation shown in the right hand column of Table 4 demonstrates that the uniformity of distribution of cesium is greatly enhanced by the catalysts prepared using PEG 4,000 compared to those examples in which PEG 4,000 was omitted. Section A is the outermost section and so on through the cylinder, E being the innermost section at the central hole.

TABLE 4

| catalyst | [Cs] solution (g/l) | [PEG 4000] g/100 ml | volume soln / volume pores | cesium content (ppm) A | B | C | D | E | normalised standard deviation |
|---|---|---|---|---|---|---|---|---|---|
| F | 2.50 | 50 | 1.1 | 885 | 870 | 665 | 670 | 790 | 0.13 |
| G | 2.86 | 50 | 1.1 | 860 | 910 | 765 | 775 | 755 | 0.08 |
| Q | 3.78 | 30 | 3.0 | 1680 | 1370 | 1090 | 1050 | 1210 | 0.20 |
| R | 3.78 | 40 | 3.0 | 1360 | 1250 | 1200 | 985 | 1100 | 0.12 |
| S | 3.78 | 50 | 3.0 | 1500 | 1300 | 1180 | 1230 | 1060 | 0.13 |
| T (comparative) | 3.78 | 0 | 3.0 | 3340 | 1560 | 1360 | 1450 | 1510 | 0.45 |

EXAMPLE 8

Cesium was added on catalyst A as described in Example 1 except that the composition of the cesium impregnation solution was 3.213 g/liter cesium supplied as the nitrate dissolved in a mixture of equal weights of water and PEG 4000. The distribution of cesium was measured as described in Example 7. The analyses are shown in Table 5. In the absence of PEG 4000 (comparative examples U, W and X) the normalised standard deviations are all high, with a large variation dependent on the anion and solvent. In the presence of PEG 4000 the distributions are uniform and independent of both solvent and cesium salt (examples V, Y and Z).

TABLE 5

| catalyst | cesium salt | [PEG 4000] % w/v | solvent | viscosity of solution × 10³ Pa s | cesium content (ppm) A | B | C | D | E | normalised standard deviation |
|---|---|---|---|---|---|---|---|---|---|---|
| U | Cs oxalate | 0 | water | 10 | 2220 | 580 | 350 | 385 | 470 | 0.89 |
| V | Cs oxalate | 50 | water | 66 | 775 | 812 | 752 | 651 | 693 | 0.08 |
| W | Cs oxalate | 0 | methanol | 0.75 | 2130 | 1050 | 1005 | 970 | 1195 | 0.34 |
| X | Cs nitrate | 0 | methanol | 0.75 | 1645 | 630 | 575 | 560 | 565 | 0.53 |
| Y | Cs nitrate | 50 | methanol | 31 | 745 | 705 | 625 | 570 | 615 | 0.10 |

EXAMPLE 9

Catalyst AA was prepared on a support composed of α-alumina containing 0.5% silica with a surface area of 2.1 m²/g and pore volume 0.3 cm³/g. The catalyst was impregnated for 20 minutes with a solution containing 0.44 g silver/cm³ composed of silver nitrate, isopropylamine (2.1 g mol/g atom silver) and water. After drainage of excess solution the catalyst was heated for 1 hour at 90° C., 1 hour at 155° C. and 1 hour at 240° C. all under a flow of nitrogen. After cooling the catalyst was washed with a flow of distilled water at 90° C. at a gas liquid space velocity of 4 liters water per kilogram catalyst per hour for 16 hours. The catalyst was dried at 120° C.

This catalyst (AA) was impregnated with different levels of potassium from solutions of potassium formate in a solution comprising methanol made up to 100 ml with 50 g PEG 4000 and 2 g water for 16 hours at room temperature. The volume of solution employed was 1.1 times that needed to fill the pores of the support. After drainage the catalysts were dried at 120° C. for 1 hour. These catalysts are designated AB, AC, AD and AE.

A second series of comparative catalysts were prepared following the method described except that PEG 4000 was omitted. These are BB, BC, BD and BE.

EXAMPLE 10

0.4 g each of catalysts prepared in Example 9 were tested for ethylene oxidation under the following gas feed at 16 bar pressure: 30% ethylene, 8% oxygen, 0.3% ethane, 5 ppm vinyl chloride, 10 ppm nitrogen dioxide, the remainder being nitrogen at a gas hourly space velocity of 3000 hr⁻¹.

The performance was measured at 20% oxygen conversion. The results are shown in Table 6.

TABLE 6

| catalyst | [potassium] (ppm) | selectivity (%) |
|---|---|---|
| AB | 500 | 81.7 |
| AC | 1000 | 87.3 |
| AD | 2000 | 85.0 |
| AE | 4000 | 81.7 |
| BB | 1000 | 84.1 |
| BC | 2000 | 85.5 |
| BD | 4000 | 82.3 |
| BE | 6000 | 71.0 |

EXAMPLE 11

Catalyst A was impregnated with solutions containing potassium formate in methanol containing variable levels of polyethylene glycol 4000 as described in Example 9. The normalised standard deviation of the radial concentrations of potassium on these catalysts determined as in Example 7 are shown in Table 7. The average concentration of potassium on the catalysts was 2000 ppm in each case.

TABLE 7

| [polyethylene glycol] (% w/w) | viscosity (Pa s) | normalysed standard deviation (%) |
|---|---|---|
| 10 | $2.4 \times 10^{-3}$ | 42 |
| 20 | $4 \times 10^{-3}$ | 38 |
| 31 | $8 \times 10^{-3}$ | 14 |
| 50 | $3.1 \times 10^{-2}$ | 11 |

EXAMPLE 12

Catalyst A was impregnated as described in Example 1 using as the impregnating solution potassium formate (6.426 g/liter) in a solution containing the specified additive in a mixture of methanol and the additive stated in Table 8 (sufficient water being added to effect the dissolution of the additive). The viscosity of the solution and the normalised standard deviation of the potassium content determined in accordance with Example 7 is shown in Table 8. The potassium content was approximately 200 ppm.

TABLE 8

| Additive | [additive] g/100 ml solution | viscosity of solution (Pa s) | normalysed standard deviation (%) |
|---|---|---|---|
| sorbitol | 50 | $1.5 \times 10^{-2}$ | 10 |
| polypropylene glycol, av mol wt = 1025 | 50 | $9 \times 10^{-3}$ | 12 |
| sucrose | 50 | $2.0 \times 10^{-2}$ | 15 |
| polypropylene glycol, av mol wt = 1025 | 85 | $3.1 \times 10^{-2}$ | 15 |

EXAMPLE 13 (Comparative)

Example 12 was repeated except that the additives therein stated were replaced by those specified in Table 9. The results are shown in Table 9. The potassium content was approximately 2000 ppm.

TABLE 9
(Comparative)

| Additive | [additive] (g/100 ml) | viscosity of solution (Pa s) | normalysed standard deviation (%) |
|---|---|---|---|
| polyethylene glycol MW = 600000 | 2.17 | $3.1 \times 10^{-2}$ | 34 |
| polyethylene glycol MW = $4 \times 10^6$ | 0.61 | $3.1 \times 10^{-2}$ | 27 |
| "Synperonic" | 0.1 | $7.5 \times 10^{-4}$ | 61 |

TABLE 9-continued (Comparative)

| Additive | [additive] (g/100 ml) | viscosity of solution (Pa s) | normalysed standard deviation (%) |
|---|---|---|---|
| A7* ethanediol | 50 | | 62 |
| " | 75 | | 73 |

*a $C_{13}/C_{15}$ alcohol condensed with 7 moles of ethylene oxide manufactured by Imperial Chemical Industries PLC owners of the trade mark "Synperonic".

In the above Examples, PEG 4000 means polyethylene glycol of mean molecular weight 4000, parts per million (ppm) means part per million of the element by weight in the analysis of solids and in the case of gases means parts per million by volume.

I claim:

1. A process in which a catalyst for the production of an alkylene oxide is produced by impregnating a composition comprising silver supported on a porous heat resisting support with a solution of an alkali metal compound in a liquid which comprises a solvent for the alkali metal compound which comprises at least 20% by weight of a component which can be converted by chemical reaction to gas or vapour only at a temperature below its boiling point or of a substance capable of forming such a component before evaporation, wherein said component is selected from the group consisting of polyethylene glycol, polypropylene glycol or a polyhydroxy compound, and removing the said component by chemical reaction, the boiling point of the said component being higher than the temperature of the said chemical reaction under the reaction conditions.

2. A process as claimed in claim 1 in which the said component has a melting point above 50° C. and a boiling point above 250° C. at atmospheric pressure.

3. A process according to claim 1 in which the viscosity of the solution is in the range $5 \times 10^{-4}$ to $5 \times 10^{-1}$ pascal seconds at the temperature of impregnation, the said temperature being in the range 15° to 40° C.

4. A process as claimed in claim 1, in which the chemical reaction converting the said component to gas or vapour is oxidation with molecular oxygen.

5. A process as claimed in claim 1 in which the boiling point of the said component is at least 50° C. higher than the temperature of the chemical reaction.

6. A process as claimed in claim 1 in which a diluent which boils at a temperature at least 50° C. lower than the said component at atmospheric pressure is present.

7. A process as claimed in claim 6 in which the diluent is a volatile solvent for the alkali metal compound selected from a $C_1$ to $C_4$ alcohol and/or water.

8. A process according to claim 1 in which the alkali metal compound is a carboxylate.

* * * * *